(12) United States Patent
Matsumoto et al.

(10) Patent No.: US 7,193,086 B2
(45) Date of Patent: Mar. 20, 2007

(54) PROCESS FOR PREPARATION OF A QUINOLINECARBALDEHYDE

(75) Inventors: Hiroo Matsumoto, Chiba (JP); Takanori Shimizu, Chiba (JP)

(73) Assignees: Nissan Chemical Industries, Ltd., Tokyo (JP); Daicel Chemical Industries, Ltd., Sakai (JP)

( * ) Notice: Subject to any disclaimer, the term of this patent is extended or adjusted under 35 U.S.C. 154(b) by 217 days.

(21) Appl. No.: 10/479,226

(22) PCT Filed: May 15, 2002

(86) PCT No.: PCT/JP02/04712

§ 371 (c)(1), (2), (4) Date: Dec. 1, 2003

(87) PCT Pub. No.: WO02/098859

PCT Pub. Date: Dec. 12, 2002

(65) Prior Publication Data

US 2004/0147750 A1 Jul. 29, 2004

(30) Foreign Application Priority Data

May 30, 2001 (JP) .............................. 2001-162986
Jul. 9, 2001 (JP) .............................. 2001-208501

(51) Int. Cl.
*C07D 215/14* (2006.01)
(52) U.S. Cl. ...................................... 546/168
(58) Field of Classification Search ................. 546/168
See application file for complete search history.

(56) References Cited

FOREIGN PATENT DOCUMENTS

| JP | 6-239779 | 8/1994 |
| JP | 8-003138 | 1/1996 |
| JP | 9-025308 | 1/1997 |

OTHER PUBLICATIONS

March , Advanced Organic Chemistry, 3$^{rd}$ Edition, pp. 1066-1067, 1985.*
(Fundamental Organic Chemistry, written by XIN, Qi-yi, published by Gaojiao Publishing Company, 2$^{nd}$ Ed., 1993, pp. 187-188.
Edited by CSJ: The Chemical Society of Japan, Jikken Kagaku Koza 21, Yuki Gosei III-Aldehyde-Keton-Quinone-, 4$^{th}$ edition, Kumao EBIHARA, pp. 51-52 Feb. 15, 1991.
J. March, "Advanced Organic Chemistry", 4$^{th}$ Edition, Reaction 9-9, p. 1177 (prior edition previously filed).

* cited by examiner

Primary Examiner—Zinna N. Davis
(74) Attorney, Agent, or Firm—Oblon, Spivak, McClelland, Maier & Neustadt, P.C.

(57) ABSTRACT

A process for producing 2-cyclopropyl-4-(4-fluorophenyl)-quinoline-3-carbaldehyde important as intermediate for the synthesis of pharmaceuticals, efficiently from an unnecessary antipode, is provided.

A process for producing 2-cyclopropyl-4-(4-fluorophenyl)-quinoline-3-carbaldehyde represented by the formula (III):

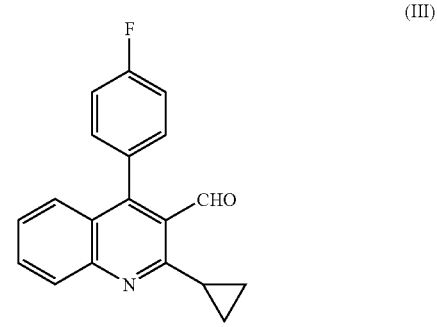

(III)

which comprises treating a compound represented by the formula (I) or (II):

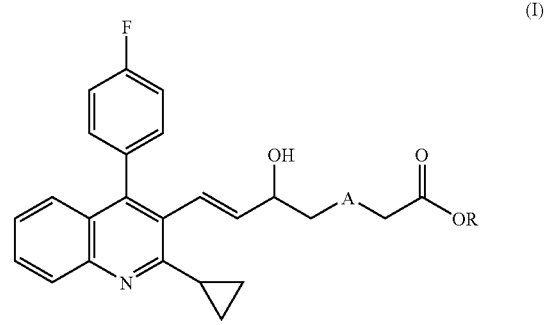

(I)

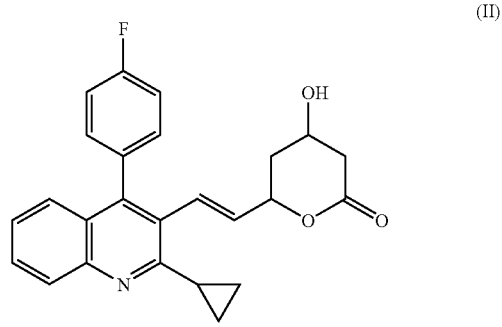

(II)

(wherein A is —CHOH— or —C(O)—, and R is a hydrogen atom, a $C_{1-4}$ alkyl group which may be branched, a phenyl group, an alkali metal ion or an alkaline earth metal ion) with ozone, followed by reduction with an inorganic sulfur compound or by hydrogenation for reduction decomposition.

8 Claims, No Drawings

PROCESS FOR PREPARATION OF A QUINOLINECARBALDEHYDE

CROSS-REFERENCE TO RELATED APPLICATIONS

The present application is a 371 application of PCT/JP02/04712 filed May 15, 2002.

TECHNICAL FIELD

The present invention relates to an economical process for producing 2-cyclopropyl-4-(4-fluorophenyl)-quinoline-3-carbaldehyde which is useful as an intermediate for the synthesis of a HMC-CoA (hydroxymethyl glutaryl CoA) reductase inhibitor as a cholesterol-reducing agent.

BACKGROUND ART

The HMG-CoA reductase inhibitor having a quinoline base nucleus can be produced by the following process as disclosed in JP-A-1-279866, EP-304063A and U.S. Pat. No. 5,011,930.

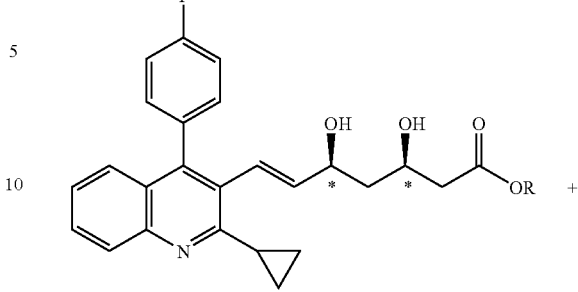

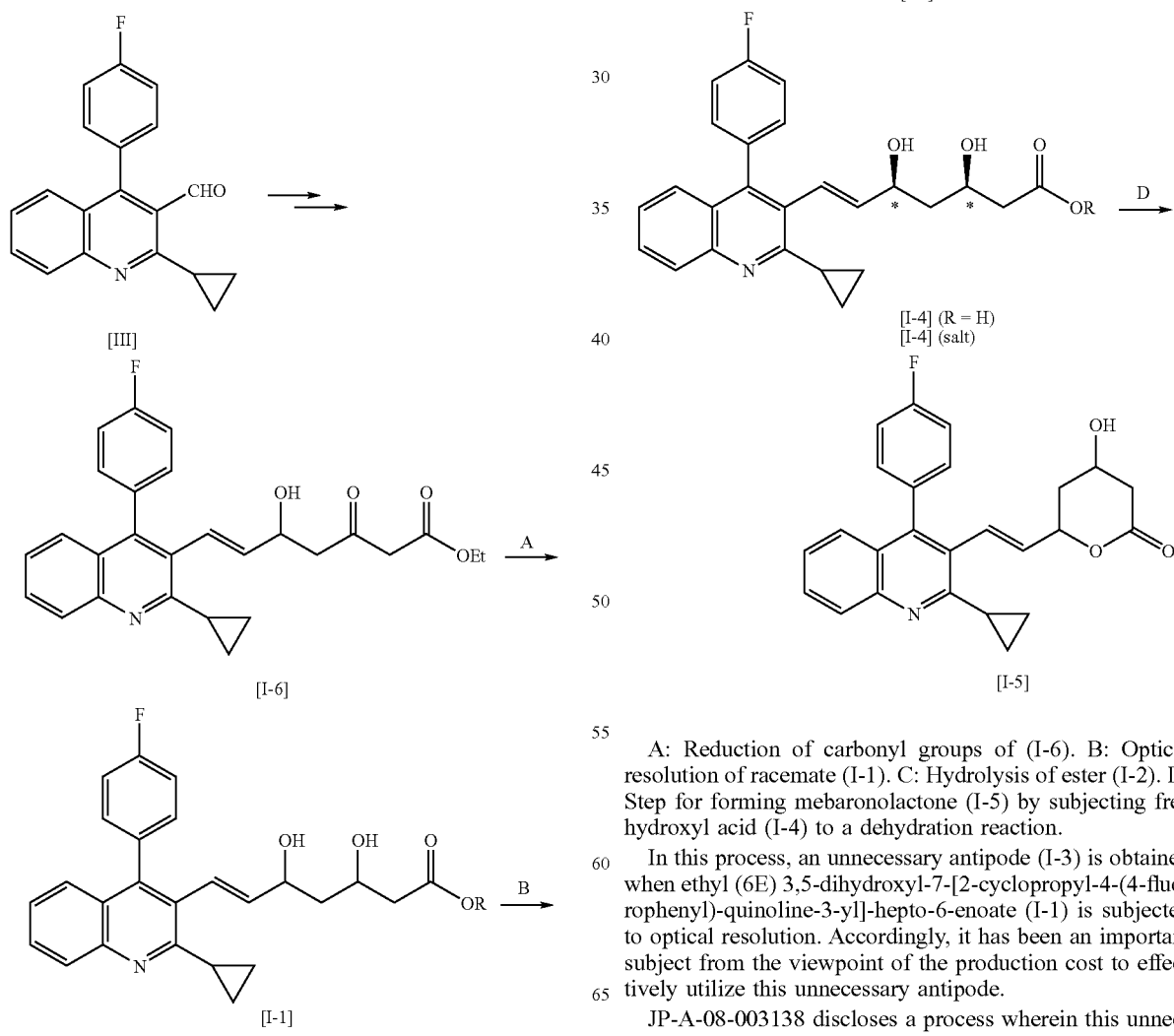

A: Reduction of carbonyl groups of (I-6). B: Optical resolution of racemate (I-1). C: Hydrolysis of ester (I-2). D: Step for forming mebaronolactone (I-5) by subjecting free hydroxyl acid (I-4) to a dehydration reaction.

In this process, an unnecessary antipode (I-3) is obtained when ethyl (6E) 3,5-dihydroxyl-7-[2-cyclopropyl-4-(4-fluorophenyl)-quinoline-3-yl]-hepto-6-enoate (I-1) is subjected to optical resolution. Accordingly, it has been an important subject from the viewpoint of the production cost to effectively utilize this unnecessary antipode.

JP-A-08-003138 discloses a process wherein this unnecessary antipode (I-3) is reacted with ozone, and the resulting ozonide (peroxide) is subjected to reducing treatment with dimethyl sulfide to obtain 2-cyclopropyl-4-(4-fluorophenyl)-quinoline-3-carbaldehyde (formula (III)) which can be re-used as an intermediate for the synthesis of the HMG-CoA reductase inhibitor.

However, dimethyl sulfide used in this process has an industrial problem due to a specific unpleasant odor and a handling problem of a low flash point compound. Accordingly, this can not be regarded as an industrially advantageous reaction.

Accordingly, it is an object of the present invention to study a reducing agent of the ozonide obtainable from the compound represented by the formula (I) or (II) and to provide a process for producing 2-cyclopropyl-4-(4-fluorophenyl)-quinoline-3-carbaldehyde industrially advantageously.

DISCLOSURE OF THE INVENTION

The present inventors have studied the process for reducing the ozonide in order to solve such problems and as a result, have found a process which is free from the above-mentioned bad odor problem or the handling problem of a low flash point compound and which is industrially advantageous with good yield and have arrived at the present invention.

Namely, the present invention relates to a process for producing 2-cyclopropyl-4-(4-fluorophenyl)-quinoline-3-carbaldehyde represented by the formula (III):

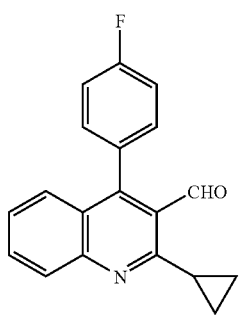

which comprises treating a compound represented by the formula (I) or (II):

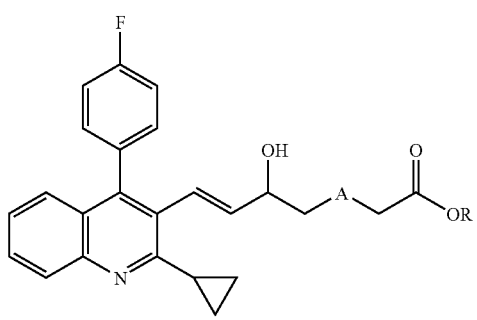

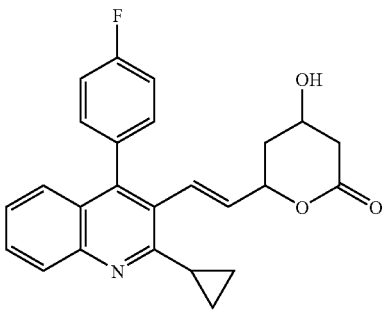

(wherein A is —CHOH or —C(O)—, and R is a hydrogen atom, a $C_{1-4}$ alkyl group which may be branched, a phenyl group, an alkali metal ion or an alkaline earth metal ion) with ozone, followed by reduction with an inorganic sulfur compound or by hydrogenation for reduction decomposition.

BEST MODE FOR CARRYING OUT THE INVENTION

Now, the present invention will be described in detail.
Firstly, terms for the substituent R will be described.
In this specification, "n" means normal, "i" iso, "s", secondary, "t" tertiary, and "c" cyclo.
As the $C_{1-4}$ alkyl group which may be branched, a methyl group, an ethyl group, a n-propyl group, an i-propyl group, a c-propyl group, a n-butyl group, an i-butyl group, a s-butyl group, a t-butyl group, a c-butyl group, a 1-methyl-c-propyl group and a 2-methyl-c-propyl group, may, for example, be mentioned.
As the alkali metal ion, a sodium ion, or a potassium ion may, for example, be mentioned.
As the alkaline earth metal ion, a calcium ion, or a magnesium ion may, for example, be mentioned. As specific R, a hydrogen atom, a methyl group, an ethyl group, a n-propyl group, an i-propyl group, a n-butyl group, an i-butyl group, a s-butyl group, a t-butyl group, a phenyl group, a benzyl group, a 1-phenylethyl group, a sodium ion, a potassium ion, a calcium ion and a magnesium ion may, for example, be mentioned, and preferably, a hydrogen atom, a methyl group, an ethyl group or an i-propyl group, a sodium ion or a calcium ion may be mentioned.
Now, the process of the present invention will be described.
The process of the present invention is one to obtain 2-cyclopropyl-4-(4-fluorophenyl)-quinoline-3-carbaldehyde represented by the formula (III) by dissolving the compound represented by the formula (I) or (II) in a solvent, then reacting ozone thereto, followed by reduction with an inorganic sulfur compound or hydrogenation for reduction decomposition preferably in the presence of a catalyst.
The compound represented by the formula (I) or (II) as the raw material can be prepared by the method disclosed in JP-A-1-279866, EP-304063A or U.S. Pat. No. 5,011,930.
It is the most convenient and excellent method to generate ozone by means of a commercially available ozone-generating apparatus and to introduce it into the reaction system as it is in the form of an ozone-oxygen stream. However, the treatment is not limited to such a method.
The amount of ozone is suitably from 0.5 to 10 equivalents, preferably from 1 to 3 equivalents, to the compound represented by the formula (I) or (II) as the raw material.

As the solvent to be used for the reaction, an alcohol such as methanol, ethanol or isopropanol, an ester such as ethyl acetate or propyl acetate, a ketone such as acetone or methyl isobutyl ketone, a cellosolve such as methoxy ethanol or ethoxy ethanol, an aprotic polar organic solvent such as dimethylformamide or tetramethylurea, an ether such as diethyl ether, diisopropyl ether, tetrahydrofuran or dioxane, an aromatic hydrocarbon such as benzene, o-dichlorobenzene, toluene or xylene, a ketone such as acetone or methyl isobutyl ketone, an alkoxy alkane such as dimethoxyethane or diethoxyethane, a nitrile such as acetonitrile or propionitrile, water and acetic acid. These solvents are suitably selected to facilitate the reaction, and may be used alone or as mixed. As a preferred solvent, an alcohol may be mentioned. More preferably, methanol, ethanol and isopropanol may be mentioned.

The amount of such a solvent is within a range of from 1 to 50 times by mass, preferably from 2 to 20 times by mass, of the compound represented by the formula (I) or (II) as the raw material.

So long as the solvent used will not be solidified, the reaction temperature is suitably within a range of from −100° C. to 100° C., preferably within a range of from −70 to 20° C.

The reaction conditions for the reduction by means of an inorganic sulfur compound will further be described.

As the inorganic sulfur compound to be used, sodium thiosulfate, sodium hydrogensulfite, sulfur dioxide or thiourea may, for example, be mentioned.

The above inorganic sulfur compounds may be suitably selected to facilitate the reaction and may be used alone or as mixed.

As a preferred inorganic sulfur compound, thiourea or sodium thiourea may, for example, be mentioned. More preferably, thiourea may, for example, be mentioned.

The amount of the inorganic sulfur compound varies depending upon the type, but is suitably from 1 to 5 equivalents, preferably from 1 to 3 equivalents, to the compound represented by the formula (I) or (II) as the raw material.

The reaction conditions for the treatment with hydrogen (hydrogenation decomposition) in the presence of a catalyst, will further be described.

With respect to the catalyst to be used, many catalyst systems may be used by combination of the metal, carrier, additives, etc. to be used.

As the metal to be used, platinum, palladium, chromium, rhodium, ruthenium or nickel, an oxide of such a metal, or an alloy of such a metal can be used.

As the carrier, silica gel, alumina, chromium oxide, diatomaceous earth, activated clay, C (activated carbon), $BaSO_4$, $CaCO_3$, $SrCO_3$, pumice and various steel chips may, for example, be mentioned.

As additives, $Pb(OAc)_2$ (lead (II) acetate) and quinoline may, for example, be mentioned.

As specific catalysts, platinum catalysts such as $PtO_2$, $PtO_2$/C, Pt/C and Pt/diatomaceous earth, palladium catalysts such as PdO, palladium black, Pd/C, Pd/$BaSO_4$, Pd/$CaCO_3$, Pd/$SrCO_3$, Pd/silica gel, Pd/$CaCO_3$—$Pb(OAc)_2$ (Lindlar catalyst) and Pd/$BaSO_4$-quinoline, chromium catalysts such as Cu—Ba—CrO and Cu—CrO, rhodium catalysts such as Rh/C and Rh/alumina, ruthenium catalysts such as $RuO_2$ and Ru/C, and nickel catalysts such as Raney Ni ($W_1$ to W8), Ni/diatomaceous earth and Ni/pumice, may, for example, be mentioned. Such catalysts may suitably be selected and may be used alone or as mixed to facilitate the reaction.

As a preferred catalyst, a palladium catalyst may be mentioned. More preferably, Pd/C and Pd/$CaCO_3$—$Pb(OAc)_2$ (Lindlar catalyst) may, for example, be mentioned.

The amount of the catalyst varies depending upon the type of the catalyst, but it is suitably from 0.001 to 1 equivalent, preferably from 0.001 to 0.1 equivalent, to the compound represented by the formula (I) or (II) as the raw material.

As the hydrogenation method, it may be carried out either under atmospheric pressure or elevated pressure.

EXAMPLES

Now, the present invention will be described in detail with reference to Examples, but the present invention is by no means restricted by these Examples.

Example 1

A methanol (50 g) solution containing 5.0 g (11.1 mmol) of ethyl (6E) 3,5-dihydroxyl-7-[2-cyclopropyl-4-(4-fluorophenyl)-quinolin-3-yl]-hept-6-enoate was cooled to 0° C., ozone gas (1 g$O_3$/hr) was introduced over a period of one hour at from 0° C. to 5° C., and then, excess ozone gas was removed by nitrogen gas. To this solution, an aqueous (14.1 g) solution of thiourea (0.85 g) was dropwise added over a period of 10 minutes at from 0° C. to 5° C., followed by stirring at the same temperature for one hour to have crystals precipitated. Further, 26 g of water was dropwise added to let crystals precipitate, followed by stirring at 5° C. for one hour, whereupon crystals were collected by filtration, washed with 6 g of 50% water-containing methanol and dried to obtain 2.81 g (yield: 86.7%) of crystals of 2-cyclopropyl-4-(4-fluorophenyl)-quinoline-3-carbaldehyde having a purity of 99.2%.

$^1$H-NMR (CDCl$_3$) δ: 1.08–1.13 (2H, m), 1.36–1.41 (2H, m), 3.18–3.26 (1H, m), 7.23–7.47 (6H, m), 7.72–7.77 (1H, m), 7.98 (1H, d, J=8.4 Hz), 10.05 (1H, S).

(Melting point: 144.0–144.3° C.).

Example 2

A methanol (50 g) solution containing 5.0 g (11.1 mmol) of ethyl (6E)3,5-dihydroxyl-7-[2-cyclopropyl-4-(4-fluorophenyl)-quinolin-3-yl]-hept-6-enoate was cooled to 0° C., ozone gas (1 g$O_3$/hr) was introduced over a period of one hour at from 0° C. to 5° C., and then, excess ozone gas was removed by nitrogen gas. To this solution, an aqueous (19.3 g) solution of sodium thiosulfate pentahydrate (4.0 g) was dropwise added. The reaction solution was heated to 12° C. and stirred for one hour to have crystals precipitated. Further, water (20 g) was dropwise added to let crystals precipitate, followed by cooling to 5° C. and stirring for one hour, whereupon crystals were collected by filtration, washed with 6 g of 50% water-containing methanol and dried. To a THF (100 ml) solution of the crystals, a 1N HCl aqueous solution (100 ml) was dropwise added and stirred at an internal temperature of 12° C. for one hour and at an internal temperature of 50° C. for two hours and then extracted with toluene (100 g) to obtain an organic layer. The aqueous layer was again extracted with toluene (50 ml), and the joined organic layer was washed with water (100 g), and then dried over anhydrous magnesium sulfate, followed by concentration under reduced pressure. To the residue, methanol (50 g) was added, and then, water (40 g) was dropwise added to let crystals precipitate, followed by stirring at 5° C. for one hour, whereupon the crystals were collected by filtration, washed with 6 g of 50% water-containing methanol and dried to obtain 2.79 g (yield: 86.2%) of crystals of 2-cyclopropyl-4-(4-fluorophenyl)-quinoline-3-carbaldehyde having a purity of 98.6%.

The $^1$H-NMR spectrum of this product agreed with that of the standard product (melting point: 145.6–145.9° C.).

Example 3

A methanol (50 g) solution containing 5.0 g (11.1 mmol) of ethyl (6E)3,5-dihydroxyl-7-[2-cyclopropyl-4-(4-fluorophenyl)-quinolin-3-yl]-hept-6-enoate was cooled to 0° C., ozone gas (1 gO$_3$/hr) was introduced over a period of one hour at from 0° C. to 5° C., and then, excess ozone gas was removed by nitrogen gas. This solution was dropwise added over a period of 10 minutes to a methanol (10 g) suspension of 10% Pd—C (0.026 g) in a hydrogen atmosphere, followed by stirring for one hour at the same temperature. The reaction solution was filtered through cerite, and the filtered product was washed with methanol (20 g). To the filtrate, 56 g of water was added to have crystals precipitated. After cooling to 5° C., stirring was carried out for one hour, whereupon the crystals were collected by filtration, washed with 6 g of 50% water-containing methanol and dried to obtain 2.83 g (yield: 87.3%) of crystals of 2-cyclopropyl-4-(4-fluorophenyl)-quinoline-3-carbaldehyde having a purity of 98.6%.

$^1$H-NMR (CDCl$_3$) δ: 1.08–1.13 (2H, m), 1.36–1.41 (2H, m), 3.18–3.26 (1H, m), 7.23–7.47 (6H, m), 7.72–7.77 (1H, m), 7.98 (1H, d, J=8.4 Hz), 10.06 (1H, S).

(Melting point: 147–148° C.).

Example 4

A methanol (50 g) solution containing 5.0 g (11.1 mmol) of ethyl (6E)3,5-dihydroxyl-7-[2-cyclopropyl-4-(4-fluorophenyl)-quinolin-3-yl]-hept-6-enoate was cooled to 0° C., ozone gas (1 gO$_3$/hr) was introduced over a period of one hour at from 0° C. to 5° C., and then, excess ozone gas was removed by nitrogen gas. This solution was dropwise added over a period of 40 minutes to a methanol (10 g) suspension of 10% Pd—C (0.15 g) in a hydrogen atmosphere. The reaction solution was heated to 20° C., stirred for 1.5 hours, then filtered through cerite, and washed with methanol (200 g). This solution was distilled under reduced pressure until the residue became 105 g. Then, 80 g of water was dropwise added to have crystals precipitated. After cooling to 5° C., stirring was carried out for one hour, whereupon the crystals were collected by filtration, washed with 6 g of 50% water-containing methanol and dried to obtain 2.03 g (yield: 62.7%) of crystals of 2-cyclopropyl-4-(4-fluorophenyl)-quinoline-3-carbaldehyde having a purity of 96.9%. The $^1$H-NMR spectrum of this product agreed with that of the standard product (melting point: 143–144° C.)

Example 5

A methanol (50 g) solution containing 5.0 g (11.1 mmol) of ethyl (6E)3,5-dihydroxyl-7-[2-cyclopropyl-4-(4-fluorophenyl)-quinolin-3-yl]-hept-6-enoate was cooled to 0° C., ozone gas (1 gO$_3$/hr) was introduced over a period of one hour at from 0° C. to 5° C., and then, excess ozone gas was removed by nitrogen gas. This solution was dropwise added over a period of 30 minutes to a methanol (10 g) suspension of a Lindlar catalyst first grade, manufactured by Wako Junyaku K. K.) (0.051 g) in a hydrogen atmosphere, followed by stirring for 30 minutes at the same temperature. Then, it was heated to 20° C. and, after adding a Lindlar catalyst (0.1 g), stirred for two hours. The reaction solution was filtered through cerite, and washed with methanol (50 g). Then, 80 g of water was dropwise added to have crystals precipitated. After cooling to 5° C., stirring was carried out for one hour, whereupon the crystals were collected by filtration, washed with 6 g of 50% water-containing methanol and dried to obtain 2.67 g (yield: 82.4%) of crystals of 2-cyclopropyl-4-(4-fluorophenyl)-quinoline-3-carbaldehyde having a purity of 97.6%. The $^1$H-NMR spectrum of this product agreed with that of the standard product (melting point: 147–148° C.).

INDUSTRIAL APPLICABILITY

According to the present invention, it is possible to produce 2-cyclopropyl-4-(4-fluorophenyl)-quinoline-3-carbaldehyde in good yield, industrially advantageously from an unnecessary antipode without a handling problem of a low flash point compound or a bad odor problem.

The invention claimed is:

1. A process for producing 2-cyclopropyl-4-(4-fluorophenyl) -quinoline-3 -carbaldehyde represented by formula (III):

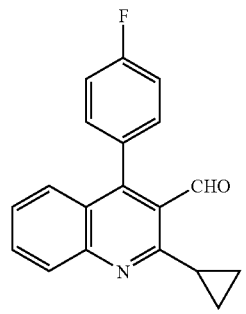

(III)

which comprises treating a compound represented by formula (I) or (II):

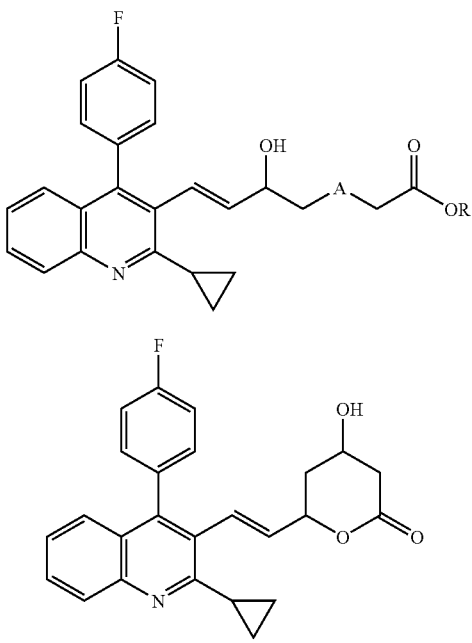

wherein A is —CHOH or —C(O)—, and R is a hydrogen atom, a $C_{1-4}$ alkyl group which may be branched, a phenyl group, an alkali metal ion or an alkaline earth metal ion with ozone, followed by reduction with at least one inorganic sulfur compound selected from the group consisting of thiourea, thiosulfate, and hydrogensulfite.

2. The process according to claim 1, wherein the compound represented by the formula (I) is ethyl (6E)3,5-dihydroxyl-7-[2-cyclopropyl-4-(4-fluorophenyl)-quinolin-3-yl]-hept-6-enoate.

3. The process according to claim 1, wherein the inorganic sulfur compound is thiourea.

4. The process according to claim 1, wherein the inorganic sulfur compound is sodium thiosulfate.

5. The process according to claim 4, wherein the palladium catalyst is a palladium catalyst having activated carbon as a carrier and represented by Pd/C.

6. The process according to claim 4, wherein the palladium catalyst is a Lindlar catalyst represented by $Pd/CaCO_3—Pb(OCH_3COO)_2$.

7. The process according to claim 1, wherein the at least one inorganic sulfur compound is thiosulfate.

8. The process according to claim 1, wherein the at least one inorganic sulfur compound is hydrogensulfite.

* * * * *